United States Patent
Han et al.

(10) Patent No.: US 10,410,822 B2
(45) Date of Patent: Sep. 10, 2019

(54) DOUBLE-TILT IN-SITU NANOINDENTATION PLATFORM FOR TRANSMISSION ELECTRON MICROSCOPE

(71) Applicant: BEIJING UNIVERSITY OF TECHNOLOGY, Beijing (CN)

(72) Inventors: Xiaodong Han, Beijing (CN); Zhipeng Li, Beijing (CN); Shengcheng Mao, Beijing (CN); Xiaodong Wang, Beijing (CN); Chunqiang Zhuang, Beijing (CN); Jianfei Zhang, Beijing (CN); Qingsong Deng, Beijing (CN); Yadi Zhai, Beijing (CN); Taonan Zhang, Beijing (CN); Ze Zhang, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 0 days.

(21) Appl. No.: 15/510,627

(22) PCT Filed: Nov. 11, 2016

(86) PCT No.: PCT/CN2016/105381
§ 371 (c)(1),
(2) Date: Jul. 14, 2017

(87) PCT Pub. No.: WO2017/054782
PCT Pub. Date: Apr. 6, 2017

(65) Prior Publication Data
US 2018/0053625 A1   Feb. 22, 2018

(30) Foreign Application Priority Data

Sep. 28, 2015 (CN) .......................... 2015 1 0629763

(51) Int. Cl.
*H01J 37/20* (2006.01)
*G01N 23/02* (2006.01)
*H01J 37/26* (2006.01)

(52) U.S. Cl.
CPC .............. *H01J 37/20* (2013.01); *G01N 23/02* (2013.01); *G01N 2223/307* (2013.01);
(Continued)

(58) Field of Classification Search
CPC .......... H01J 2237/206; H01J 2237/262; H01J 2237/20207; H01J 2237/2007;
(Continued)

(56) References Cited

U.S. PATENT DOCUMENTS 6,817,255 B2 * 11/2004 Haque .................... H01L 22/34
73/626
7,752,916 B2 * 7/2010 Han ........................ G01N 3/04
73/789
(Continued)

FOREIGN PATENT DOCUMENTS

CN          1963985 A      5/2007
CN        101221105 A      7/2008
(Continued)

OTHER PUBLICATIONS

Chinese International Search Report of corresponding International PCT Application No. PCT/CN2016/105381, dated Jan. 23, 2017.
(Continued)

*Primary Examiner* — Wyatt A Stoffa
(74) *Attorney, Agent, or Firm* — J.C. Patents

(57) ABSTRACT

A double-tilt in-situ nanoindentation platform for TEM (transmission electron microscope) belongs to the field of in-situ characterization of the mechanical property-microstructure relationship of materials at the nano- and atomic scale. The platform is consisted of adhesive area, support
(Continued)

Figure 1:
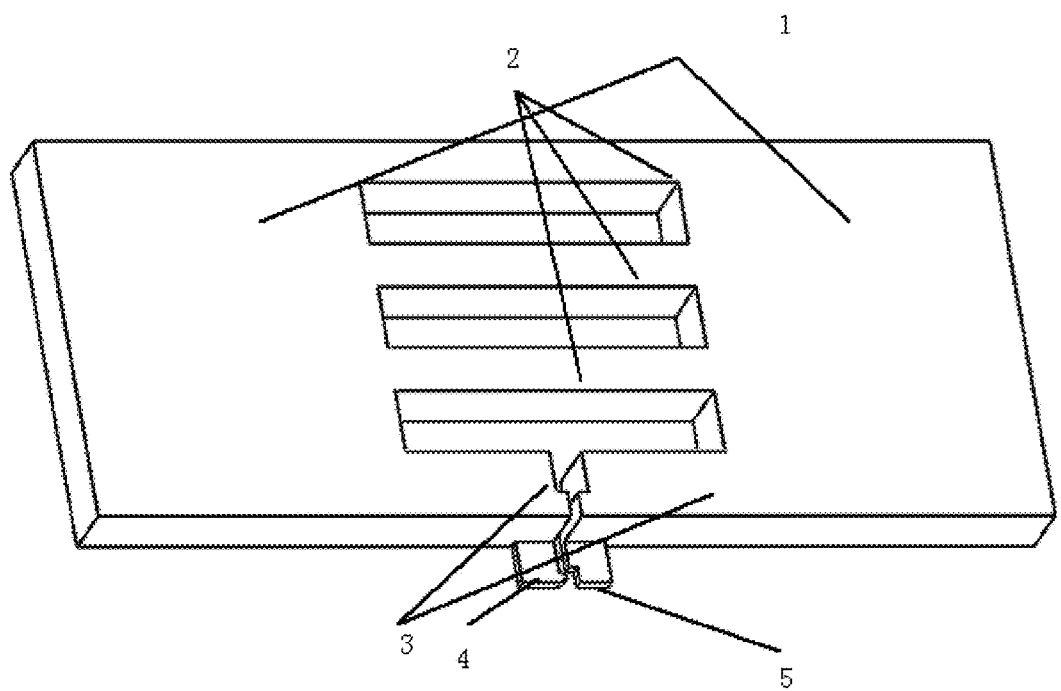

beams, bearing beams, sample loading stage and mini indenter. The overall structure of the platform is prepared by semiconductor microfabrication technology. The in-situ nanoindentation experiment can be driven by bimetallic strip, V-shaped electro-thermal beam, piezoelectric ceramics, electrostatic comb or shape memory alloys et. al. The sample is obtained by focused ion beam cutting. The integrated platform can be placed in the narrow space on the front end of the TEM sample holder, giving rise to the condition of double-axis tilt. The driving device drives the mini indenter to carry out in-situ nanoindentation, in-situ compression and in-situ bending and the like of the materials in TEM. The deformation process of material can be in-situ observed in sub angstrom, atomic and nano scale to study the deformation mechanism of material, which can further reveal the relationship of microstructure-mechanical properties of the material.

14 Claims, 3 Drawing Sheets

(52) U.S. Cl.
CPC ... *G01N 2223/32* (2013.01); *G01N 2223/418* (2013.01); *H01J 37/26* (2013.01); *H01J 2237/206* (2013.01); *H01J 2237/2007* (2013.01); *H01J 2237/262* (2013.01)

(58) Field of Classification Search
CPC ....... H01J 2237/202; H01J 2237/20214; H01J 2237/20264; H01J 37/20; H01J 37/26; G01N 2203/0286; G01N 23/02; G01N 2223/32
See application file for complete search history.

(56) References Cited

U.S. PATENT DOCUMENTS

| | | | | |
|---|---|---|---|---|
| 8,089,053 B1* | 1/2012 | Finch | ...................... | H01J 37/20 250/440.11 |
| 8,499,645 B2* | 8/2013 | Chasiotis | ............... | G01N 19/04 73/789 |
| 9,741,527 B2* | 8/2017 | Vystavel | ................. | H01J 37/16 |
| 2005/0103996 A1* | 5/2005 | Olin | ....................... | B82Y 35/00 250/311 |
| 2007/0180924 A1* | 8/2007 | Warren | .................... | G01B 7/22 73/780 |
| 2008/0276727 A1 | 11/2008 | Enoksson et al. | ......... | 73/862.68 |
| 2010/0017921 A1* | 1/2010 | Rangelow | .............. | B82Y 35/00 850/1 |
| 2010/0064765 A1* | 3/2010 | Han | ........................ | G01N 3/04 73/1.15 |
| 2010/0095780 A1* | 4/2010 | Oh | ........................ | B81C 99/005 73/774 |
| 2010/0281963 A1 | 11/2010 | Greer | ............................... | 73/82 |
| 2013/0098144 A1* | 4/2013 | Oh | .......................... | G01N 3/42 73/81 |
| 2013/0098145 A1* | 4/2013 | Oh | .......................... | G01N 3/42 73/81 |
| 2014/0013854 A1* | 1/2014 | Kang | .................... | B81C 99/005 73/774 |
| 2015/0369839 A1* | 12/2015 | Beyeler | ................. | G01Q 20/00 850/5 |
| 2016/0282246 A1* | 9/2016 | Yang | ....................... | G01M 5/00 |

FOREIGN PATENT DOCUMENTS

| | | |
|---|---|---|
| CN | 102262996 A | 11/2011 |
| CN | 102288501 A | 12/2011 |
| CN | 201320574347.8 | 9/2013 |
| CN | 203443871 U | 2/2014 |
| CN | 103645199 A | 3/2014 |
| CN | 203534987 U | 4/2014 |
| CN | 104198663 A | 12/2014 |
| CN | 104634660 A | 5/2015 |
| CN | 204558415 U | 8/2015 |
| CN | 105223213 A | 1/2016 |
| JP | 2005-509864 A | 4/2005 |

OTHER PUBLICATIONS

Bobji, M. S. et al., "A miniaturized TEM nanoindenter for studying material deformation in situ" Measurement Science and Technology; vol. 17, No. 6; (May 2006); pp. 1324-1329.
Kiritani, M. et al., "Anomalous production of vacancy clusters and the possibility of metals plastic deformation of crystalline metals without dislocations" Philosophical Magazine Letters; vol. 79, No. 10; (1999); pp. 797-804.
Lockwood, A. J. et al., "Advanced transmission electron microscope triboprobe with automated closed-loop nanopositioning" Measurement Science and Technology; vol. 21, No. 7; (2010); 7 pages.
Stach, Eric A. et al., "Development of a Nanoindenter for In Situ Transmission Electron Microscopy" Microscopy and Microanalysis; vol. 7, Issue 6; (2001); pp. 507-517.
Wall, M. A. et al., "An in-Situ Nanoindentation Specimen Holder for a High-Voltage Transmission Electron Microscope" Microscopy Research and Technique; vol. 42, Issue 4; (1998); pp. 248-254.
Yu, Qian et al., "Strong crystal size effect on deformation twinning" Nature; vol. 463; (Jan. 21, 2010); nature08692.
Zheng, He et al., "Discrete plasticity in sub-10-nm-sized gold crystals" Nature Communications; Article No. 144; (Nov. 25, 2010); ncomms1149.
The Chinese First Examination Report of corresponding Chinese patent application No. 201510629763.7, dated Aug. 23, 2017.

* cited by examiner

DOUBLE-TILT IN-SITU NANOINDENTATION PLATFORM FOR TRANSMISSION ELECTRON MICROSCOPE

TECHNICAL FIELD

The invention relates to a platform for the experiments of in-situ nanoindentation, compression and bending of materials for transmission electron microscope (TEM) under the condition of double-axis tilt. Using this platform, the observation of the microstructure evolution can be conducted in TEM in sub angstrom, nano and atomic scale during sample deformation. The patent belongs to the field of in-situ characterization of the relationship of mechanical property-microstructure of materials in TEM.

BACKGROUND ART

The properties of nanomaterials are different from their bulk counterparts when the characteristic dimension is reduced to nano and atomic level. For example, In *Anomalous production of vacancy clusters and the possibility of plastic deformation of crystalline metals without dislocations* Kiritani et al. found that the deformation of face-centered-cubic structure bulk materials is realized mainly through dislocation glide, while the deformation of face-centered-cubic structure thin film in nano scale is closely related to the substantial amount of vacancies inside the material; In *Discrete plasticity in sub-10-nm-sized gold crystals* Zheng et al. found that the mechanism dominating plastic deformation is the nucleation of partial dislocation in single crystal gold with dimensions less than 10 nm, different from the mechanism of plastic deformation dominated by the Frank-Read source in gold bulk materials; In *Strong crystal size effect on deformation twinning* Yu et al. found that for titanium alloy single crystal the stress required for deformation twinning increases drastically with decreasing sample size. It is of great theoretical and practical importance to study the deformation mechanism of materials and its influence on the mechanical properties for further development of materials with high performance.

The microstructure of materials in sub angstrom, nanometer and atomic scale can be studied by TEM. The latest spherical aberration correction transmission electron microscope can study the microstructure of materials with a spatial resolution of less than 0.1 nm. Apart from the static characterization of microstructures, researchers and manufacturers around the world have developed different kinds of TEM in situ characteristic techniques to study the correlation between the microstructure of materials and their mechanical, thermal, electrical, optical, and various kinds of coupling properties. These developments have greatly enriched the characterization ways in revealing all kinds of physical mechanism of materials. Among these in-situ deformation techniques, the in-situ mechanical measurement of nanomaterials has been widely payed attention to, because that the stability and service life of the materials are mainly determined by their mechanical properties. Using the in-situ mechanical testing, it is easy to study the microstructural evolution of materials under the condition of external force which can guide the understanding of the elastic/plastic deformation mechanism of materials.

At present, the loads applied in in-situ mechanical experiment in TEM are usually tensile load and compressive load. Compared to tensile load, compressive load is more applicable in the study on brittle materials such as ceramics, since brittle materials will break after the yield point under tensile load, which makes it impossible to in situ observe the process of plastic deformation and in turn hinters the precise analysis of materials' deformation mechanism.

In-situ nanoindentation/compression experiment in TEM has obvious advantages compared to ex-situ TEM experiment in which observation and analysis is carried out after unloading. In the ex-situ experiment, the evolution of microstructure can not be observed when the indenter is pressed in, thus it is hard to deduce the correlation between the microstructure and mechanical properties of materials by the fragmented microstructure. The evolution of microstructure during the overall process of indenter pressed—stay—withdrawal can be observed and analyzed in real time by in-situ nanoindentation, thus provides high chance to study the relationship of microstructure-mechanical properties in sub angstrom, atomic and nano scale.

In the present studies, in-situ nano compression/indentation experiments were mainly carried out by commercial in-situ nano compression/indentation TEM holder. In the paper *An in-situ nanoindentation sample holder for a high-voltage TEM* (year 1998), Wall et al. designed the first generation of in-situ nanoindentation sample holder applicable to high-voltage TEM, in which detachable sample loading stage and piezoelectric driving indenter were used. The indenter was first adjusted to a certain range from the sample by a coarse positioning device of gear motor, and then was further driven to get close to and pressed into the sample by a piezoelectric ceramics driver. In the paper *development of a nanoindenter for in-situ TEM* (year 2001), Stach et al. applied the sample holder to low-voltage electron microscope, and at the same time improved the displacement resolution of the indenter, making the press-in process more stable and controllable. Svensson et al. eliminated the vibration generated during the coarse positioning by using displacement accumulation of piezoelectric ceramics. In the paper *A miniaturized TEM nanoindenter for studying material deformation in-situ* (year 2006), Bobji et al. further improved the control of press-in track by coupling a signal sensor with controllable flexure hinge, by which the force-displacement curve in the press-in process could be obtained. The indenter in the above in-situ nanoindentation experiments was in tapered shape with curvature radius of tens to hundreds of nanometer. The thickness of the TEM sample was also tens to hundreds of nanometer. Therefore, it is hard to exactly control the contact of the indenter and the sample, thus it is time consuming to conduct the indentation and compression tests in TEM. In the paper *Advanced TEM triboprobe with automated closed-loop nanopositioning* (year 2010), Lockwood et al. developed an image feedback system to precisely positioning the indenter and the specimen, thus greatly improved the efficiency of in-situ experiment.

Some of the compression/indentation TEM holders have been commercialized by Hysitron, Nanofactory companies and etc. and have been successfully applied to the study of the mechanical properties structure relationship of materials under indentation and compression. Until now, all the commercial holders are driven by piezoelectric ceramics, which can only be placed in the middle or front of sample holder because of its relatively large volume, which disables the Y-axis tilt of the holder and limits the obtaining of the evolution of microstructure at atomic and sub angstrom scale. In the patent A double-axis tilt in-situ nanoindentation device for TEM (patent application number: 201320574347.8), Han et al. designed a platform by which in-situ nanoindentation under the condition of double-axis tilt can be realized in TEM. The design is simple and low-cost, but it is difficult to precisely positioning the indenter as close and parallel as possible to the specimen.

This invention designs a platform for in-situ nanoindentation experiment under the condition of double-axis tilt for TEM. This technique is simple and applicable for mass production. With this technique, we can conduct nanoindentation, compression and bending of the sample and simultaneously obtain the evolution of microstructure at nano, atomic and sub-angstrom scale, which provides an advantageous tool to reveal the deformation mechanism of the materials.

CONTENTS OF THE INVENTION

Aiming at resolving the various problems exist in the present in-situ nanoindentation/compression platform for TEM, the invention designs a platform for in-situ nanoindentation experiment under the condition of double-axis tilt in TEM, the technique of which is simple and applicable for mass production, by which nanoindentation, compression and bending of the sample can be realized, and at the same time the microstructure evolution in the process of deformation can be in-situ recorded by TEM, which provides an advantageous tool revealing the deformation mechanism of the materials.

The double-tilt in-situ nanoindentation/compression platform for TEM is prepared by semiconductor microfabrication technology. The force/displacement driver can be bimetallic strips, V-shaped electro thermal beam, piezoelectric ceramics, electrostatic comb and shape memory alloys and the like. The samples used for indentation/compression are prepared by focused ion beam.

Take bimetallic strips driver as an example, the integrated platform is bonded onto the bimetallic strips and integrally placed on the loading stage at the front end of the double-axis tilt heating sample holder. Upon heating by the heating crucible on the sample holder, the bimetallic strips drive the indenter to press in/compress the sample gradually under the condition of double-axis tilt, thus can in-situ observe the evolution of microstructure at nano, atomic and sub angstrom scale.

The invention fills the blank that current nanoindentation/ compression TEM holders cannot conduct the experiments under the double-axis tilt, and thus cannot in situ observe the evolution of microstructure at nano, atomic and sub angstrom scale. Moreover, the relative position of the indenter and the sample loading stage is pre-fixed in such a way that the indentation can be realized by simply driving the indenter in one direction back and forth.

At the same time the observation of microstructure evolution of materials in sub angstrom, nano and atomic scale is helpful to reveal the deformation mechanism of materials under pressure and establish corresponding atomic model.

The ways to realize the above purpose in the invention are as follows:

A double-tilt in-situ nanoindentation platform for TEM, characterized in that: it include adhesive area, support beam, bearing beam, sample loading stage and mini indenter of five parts; therein, adhesive area is rectangular plate area located symmetrically on both sides; support beam are 2~4 rectangular champed beams, connecting the adhesive area on both sides; bearing beam are two cantilever beams designed symmetrically, one side of each cantilever beam respectively connecting adhesive area and the other side reaching out to the center of the device; sample loading stage is a plate, the tail end connecting the end of bearing beam, and a gap is cut on the side close to the mini indenter as electron beam permeation area; mini indenter is a rectangular plate, the tail end connecting the other bearing beam, and a triangular tine is at the side close to the sample loading stage.

Further, the thickness of the said adhesive area is 5~100 µm, and the length and width of which are 50~200 µm and 5~200 µm respectively, which are used to bond to the driver.

Further, the thickness of the said support beam is 5~100 µm, and the length and width of which are 30~200 µm and 5~50 µm respectively, which are used to connect the adhesive area on both sides.

Further, the thickness of the said bearing beam is 5~100 µm, and the length and width of which are 10~200 µm and 5~100 µm respectively, the free end of which bears mini indenter and sample loading stage respectively.

Further, the said mini indenter connects the free end of one bearing beam, and the thickness of which is 1~10 µm.

Further, the said sample loading stage connects the free end of the other bearing beam, and the thickness of which is 1~10 µm, and the gap from mini indenter is 2~20 µm, which is used to carry the sample.

Further, the said platform is prepared by the semiconductor microfabrication and integral forming technology, and can be formed by one time, the common materials in micro electro mechanical system like silicon, silicon carbide, diamond, GaAs and quartz crystal and like are selected.

Further, the platform can be driven by the selection of hot bimetallic strips, V-shaped electro thermal beam, piezoelectric, electrostatic, electromagnetic or memory alloy and like.

The said platform for double-axis tilt in-situ nanoindentation/compression experiment for TEM in the patent include adhesive area, support beam, bearing beam, sample loading stage and mini indenter of five parts. The said adhesive area is the region both sides of which is used to bond the driver; the said support beam connect the adhesive area on both sides, used to ensure the relative position of indenter and loading stage unchanging; the said bearing beam is located at the upper edge of the device, connecting the adhesive area;

The said indenter and sample loading stage are respectively located at the free sides of the two bearing beams. The thickness of adhesive area and bearing beam should be adjusted according to the mechanical stress supported in the process of the use of integrated platform, ensuring the structure steady. The thickness of the bearing beam should be stable sufficiently to bear sample loading stage and mini indenter. The thickness of sample loading stage and mini indenter are thinner, to reduce the shelter of electron beam from double-axis tilt. When the thickness of adhesive area, support beam and bearing beam are more than 10 µm, the sample loading stage and mini indenter should be edge dropped separately, to less than 10 µm.

Specifically, when the overall thickness of the platform is less than 10 µm, its processing technique include two-time photolithography: the first is front mechanical structure etching, etching down the overall appearance of the device; for the second time etching from the back, releasing windows, forming the integrated platform. When the overall thickness of the platform is more than 10 µm, the processing technology include three-time photolithography: the first is edge-drop of front mini indenter and sample loading stage, etching a certain height of steps from above down, ensuring the final thickness of less than 10 µm; the processes of second and third photolithography are same with that when overall thickness of platform is less than 10 µm.

The said adhesive area is a symmetric flat plate region located on the left and right sides of the device, with the length of 5~200 µm, the width of 5~200 µm, and the thickness of 5~100 µm. Take hot bimetallic strips drive as an example, when in use, the two bimetallic strips are first fixed in parallel on copper back-up ring with the outer diameter of 3 mm, and the metal with a smaller thermal expansion coefficient is at the inside, and the free ends of the two metal strips get close to each other when heated. Two adhesive area are symmetrically fixed on the hot bimetallic strips on both sides by AB glue, making the front end of the device flush with the free end of the bimetallic strips. The said 2~4 support beams connect with the adhesive area on left and right side, with the length of 30~200 µm, with the width of 5~50 µm, and the thickness of 5~100 µm. After the adhesion is steady, all the support beams are cut off. The said two bearing beams are cantilever beams, with the length of 10-100 µm and the width of 5-100 µm and the thickness of 5-100 µm, located at the upper edge of the device, one end of which connects with the adhesive area on the same side, and the other end reaches out to the middle of the device is free, used for bearing mini indenter and sample loading stage. The said mini indenter connects with the free end of the bearing beam, and its thickness is 1~10 µm. The said sample loading stage connects the free end of the other bearing beam, and its thickness is 1~10 µm. The distance of the mini indenter and sample loading stage is 2~20 µm. The sample is welded on the sample loading stage by the focused ion beam technique.

The temperature of bimetallic strips driver is controlled by changing the heating current of heating holder; the free ends get bent in the process of heating because two kinds of metals in the bimetallic strips have different thermal expansion coefficients, close to each other, driving the indentation/compression indenter and sample loading stage get close to each other, until the indenter is pressed into thin area. The depth and speed of the indenter pressed-in can be adjusted by controlling the heating rate. The change of the microstructure of the thin area in the process of press-in can be observed and recorded in real time by the TEM observation screen or CCD camera.

Other TEM in-situ mechanical experiments like in-situ compression and in-situ bending and like can be realized by changing the size and shape of the indenter and the sample. The front end of the indenter used in indentation experiment is designed as wedge shape, and the shape of corresponding sample is designed as flaky shape; the indenter used for compression or bending is designed as flat-head shape, in square or rectangular. The corresponding sample is designed as column shape, and its sectional area is less than that of flat-head indenter.

The in-situ tensile test of the sample can be carried out on the platform by changing the bonding direction of bimetallic strips drive and getting two free ends separated from each other.

The invention has the following advantages:
1. The invention provides a platform for in-situ nanoindentation experiment under the condition of double-tilt for TEM, and it fills the gap double-tilt in-situ indentation experiment in TEM can not be realized.
2. The in-situ nanoindentation platform for TEM related in the invention can be driven in many kinds of ways. The method of drive and control is simple when bimetallic strips driving is selected. The established in-situ nanoindentation system can be directly used coordinating with commercial TEM heating holder, and the operation is convenient.
3. The in-situ nanoindentation platform for TEM related in the invention provides suitable position relationship of indenter and sample, and indention, compression, bending experiments can be realized only by controlling the drive system to drive indenter and sample in one dimension direction, improving the work efficiency and success rate of the experiment.
4. The temperature range of the experiment on in-situ nanoindentation platform for TEM related in the invention can be preset when the sample is carried with focused ion beam, which meet the requirements of the force and thermal coupling experiment to a certain extent.

DESCRIPTION OF APPENDED DRAWINGS

FIG. 1 is the schematic diagram of the double-tilt in-situ nanoindentation platform for TEM.

Figure 2:
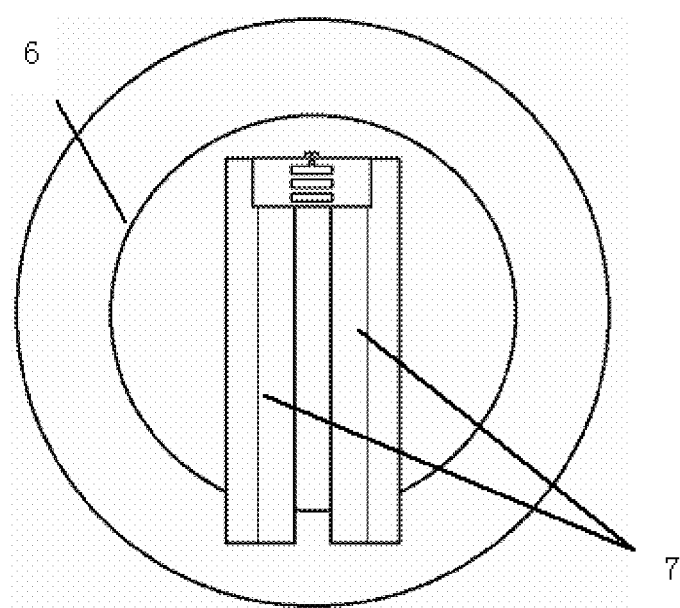

The surfaces in the diagram are illustrated as follows
1 adhesive area 2 support beam 3 bearing beam 4 mini indenter 5 sample loading stage FIG. 2 is the assembly diagram of the double-tilt in-situ nanoindentation platform and the bimetallic strips driver for TEM.

Figure 3:
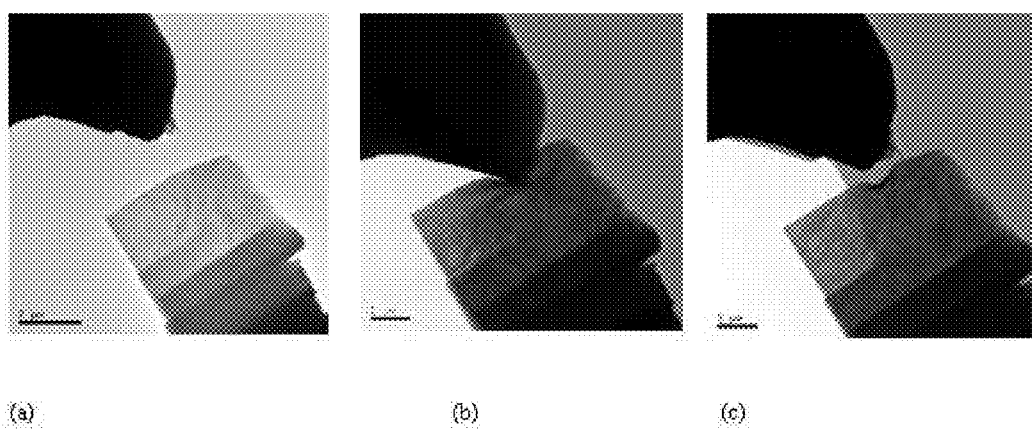

The surfaces in the diagram are illustrated as follows
6 copper back-up ring 7 bimetallic strips FIG. 3 is the photo of in-situ nanoindentation experiment (a) before the indenter pressed; (b) the process of the indenter pressed; (c) after the indenter withdrawn.

DESCRIPTION OF THE PREFERRED EMBODIMENTS

The patent is further illustrated combining FIG. 1 and FIG. 2:

Specific method of preparation: using semiconductor microfabrication technology, when the overall thickness of the platform was more than 10 µm, the photolithography was processed by three times: dry etching was used in the first photolithography, first the area that sample loading stage and mini indenter locate was etched down to a certain depth from the front side, ensuring the final thickness of the area of less than 10 µm; dry etching was used in the second photolithography, etching the overall structure of integrated platform downward from the front side; wet etching was used in the third photolithography, releasing windows upward from the back side, etching until the device was suspended. When the overall thickness of the platform was less than 10 µm, only last two step photolithography should be carried out.

Specific method of use: take bimetallic strips drive as an example, put the functional area of the device upward and bonded it to the front end of inward bimetallic strips driver bonded on the passive end; the support beam was cut off after the bonding was steady, getting both sides of indenter and sample loading stage separated completely; the sample was taken out, bonded to the loading stage and edge dropped by focused ion beam technique.

Specific method of experiment: the above in-situ nanoindentation platform for TEM carrying the sample was enclosed into the double-tilt heating sample holder for TEM and inserted into TEM, and the sample was tilted to the ideal angle, and the driving part could be heated while the TEM was in the mode of bright field, dark field or selected area diffraction etc. The deformation process of the sample under the effect of the indenter was in real-time observed and recorded.

What is claimed is:
1. A double-tilt in-situ nanoindentation platform for transmission electron microscope (TEM), comprising: an adhesive area, support beams, bearing beams, a sample loading stage and a mini indenter; wherein two ends of each of the support beams are connected to the adhesive area, respec- tively; the bearing beams comprise two cantilever beams symmetrically designed, and one end of each of the cantilever beams is respectively connected to the adhesive area and a free end of each of the cantilever beams extends towards a center of the double-tilt in-situ nanoindentation platform; the sample loading stage is a plate with its rear end connecting to the free end of one of the cantilever beams, and a notch is formed on a front end of the sample loading stage facing the mini indenter for penetration of an electron beam; the mini indenter is a plate with a thickness of 1-10 μm and with its rear end connecting to the free end of the other cantilever beam, and a tine is formed on a front end of the mini indenter facing the sample loading stage.

2. The double-tilt in-situ nanoindentation platform for TEM according to claim 1, wherein the adhesive area is of a rectangular shape with a thickness of 5-100 μm, a length of 50-200 μm and a width of 50-200 μm respectively.

3. The double-tilt in-situ nanoindentation platform for TEM according to claim 1, wherein the support beams are rectangular beams with a thickness of 5-100 μm, a length of 30-200 μm and a width of 5-50 μm respectively.

4. The double-tilt in-situ nanoindentation platform for TEM according to claim 1, wherein the bearing beams are rectangular beams with a thickness of 5-100 μm, a length of 10-200 μm and a width of 5-100 μm respectively.

5. The double-tilt in-situ nanoindentation platform for TEM according to claim 1, the sample loading stage has a thickness of 1-10 μm, and a gap between the front end of the sample loading stage and the front end of the mini indenter is 2-20 μm.

6. The double-tilt in-situ nanoindentation platform for TEM according to claim 1, wherein the double-tilt in-situ nanoindentation platform is prepared by semiconductor microfabrication technology, and made of materials selected from silicon, silicon carbide, diamond, GaAs and quartz crystal.

7. The double-tilt in-situ nanoindentation platform for TEM according to claim 1, the double-tilt in-situ nanoindentation platform is driven by bimetallic strip, V-shaped electro thermal beam, piezoelectric ceramics, electrostatic comb or shape memory alloys.

8. A double-tilt in-situ nanoindentation platform for transmission electron microscope (TEM), comprising: an adhesive area, support beams, bearing beams, a sample loading stage and a mini indenter; wherein two ends of each of the support beams are connected to the adhesive area, respectively; the bearing beams comprise two cantilever beams symmetrically designed, and one end of each of the cantilever beams is respectively connected to the adhesive area and a free end of each of the cantilever beams extends towards a center of the double-tilt in-situ nanoindentation platform; the sample loading stage is a plate with its rear end connecting to the free end of one of the cantilever beams, and a notch is formed on a front end of the sample loading stage facing the mini indenter for penetration of an electron beam; the mini indenter is a plate with its rear end connecting to the free end of the other cantilever beam, and a tine is formed on a front end of the mini indenter facing the sample loading stage;

wherein the sample loading stage has a thickness of 1-10 μm, and a gap between the front end of the sample loading stage and the front end of the mini indenter is 2-20 μm.

9. The double-tilt in-situ nanoindentation platform for TEM according to claim 8, wherein the adhesive area is of a rectangular shape with a thickness of 5-100 μm, a length of 50-200 μm and a width of 50-200 μm respectively.

10. The double-tilt in-situ nanoindentation platform for TEM according to claim 8, wherein the support beams are rectangular beams with a thickness of 5-100 μm, a length of 30-200 μm and a width of 5-50 μm respectively.

11. The double-tilt in-situ nanoindentation platform for TEM according to claim 8, wherein the bearing beams are rectangular beams with a thickness of 5-100 μm, a length of 10-200 μm and a width of 5-100 μm respectively.

12. A double-tilt in-situ nanoindentation platform for transmission electron microscope (TEM), comprising: an adhesive area, support beams, bearing beams, a sample loading stage and a mini indenter; wherein two ends of each of the support beams are connected to the adhesive area, respectively; the bearing beams comprise two cantilever beams symmetrically designed, and one end of each of the cantilever beams is respectively connected to the adhesive area and a free end of each of the cantilever beams extends towards a center of the double-tilt in-situ nanoindentation platform; the sample loading stage is a plate with its rear end connecting to the free end of one of the cantilever beams, and a notch is formed on a front end of the sample loading stage facing the mini indenter for penetration of an electron beam; the mini indenter is a plate with its rear end connecting to the free end of the other cantilever beam, and a tine is formed on a front end of the mini indenter facing the sample loading stage;

wherein the bearing beams are rectangular beams with a thickness of 5-100 μm, a length of 10-200 μm and a width of 5-100 μm respectively.

13. The double-tilt in-situ nanoindentation platform for TEM according to claim 12, wherein the adhesive area is of a rectangular shape with a thickness of 5-100 μm, a length of 50-200 μm and a width of 50-200 μm respectively.

14. The double-tilt in-situ nanoindentation platform for TEM according to claim 12, wherein the support beams are rectangular beams with a thickness of 5-100 μm, a length of 30-200 μm and a width of 5-50 μm respectively.

* * * * *